(12) United States Patent
Brush et al.

(10) Patent No.: US 7,223,538 B2
(45) Date of Patent: May 29, 2007

(54) POST-SYNTHESIS LABELING OF NUCLEIC ACIDS, ASSAYS USING NUCLEIC ACIDS THAT ARE LABELED POST-SYNTHETICALLY, SINGLE NUCLEOTIDE POLYMORPHISM DETECTION, AND ASSOCIATED COMPOUNDS AND MICROARRAYS

(75) Inventors: Charles K. Brush, Whitefish Bay, WI (US); Vineet Gupta, Brookline, MA (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 521 days.

(21) Appl. No.: 10/022,014

(22) Filed: Dec. 14, 2001

(65) Prior Publication Data

US 2003/0119005 A1    Jun. 26, 2003

(51) Int. Cl.
*C12Q 1/68* (2006.01)
(52) U.S. Cl. .......................................... 435/6
(58) Field of Classification Search .................... 435/6, 435/7.1, 91.1, 91.2, 287.2; 536/22.1, 23.1, 536/24.3–24.33
See application file for complete search history.

(56) References Cited

U.S. PATENT DOCUMENTS

| | | | |
|---|---|---|---|
| 4,908,307 A | | 3/1990 | Rodland et al. |
| 5,348,633 A | * | 9/1994 | Karger et al. ............... 204/452 |
| 5,545,531 A | | 8/1996 | Rava et al. |
| 5,702,925 A | | 12/1997 | Smith et al. |
| 5,741,644 A | | 4/1998 | Kambara et al. |
| 5,804,375 A | | 9/1998 | Gelfand et al. |
| 5,830,655 A | * | 11/1998 | Monforte et al. ............... 435/6 |
| 5,857,659 A | | 1/1999 | Kato et al. |
| 6,087,095 A | | 7/2000 | Rosenthal et al. |
| 6,120,997 A | * | 9/2000 | Wong et al. .................... 435/6 |
| 6,183,970 B1 | | 2/2001 | Okano et al. |

FOREIGN PATENT DOCUMENTS

| | | |
|---|---|---|
| WO | WO 98/29736 | 7/1998 |
| WO | WO 98/56954 | 12/1998 |
| WO | WO 00/39345 | 7/2000 |
| WO | WO 00/79006 A1 | 12/2000 |

OTHER PUBLICATIONS

Housby et al. When is a chip not a chip? TIBTECH, vol. 18, pp. 439-440, Nov. 2000.*
Zoeller et al. The Journal of Histochemistry & Cytochemistry, vol. 45, No. 7, pp. 1035-1041, 1997.*
Yang et al. Genome Research, vol. 11, pp. 1888-1898, Nov. 7, 2001.*
Conway, Nancy E. et al., "The Covalent Attachment of Multiple Fluorophores to DNA Containing Phosphorothioate Diesters Results in Highly Sensitive Detection of Single-Stranded DNA", Bioconjugate Chem., vol. 2, No. 6, 1991, pp. 452-457.
Eckstein, F., "Nucleoside Phosphorothiates", Ann Rev. Biochemistry, vol. 54, 1985, pp. 367-402.
Fidanza, Jacqueline A. et al., "Introduction of Reporter Groups at Specific Sites in DNA Containing Phosphorothioate Diesters", Am. Chem. Soc., vol. 111, 1989, pp. 9117-9119.
Fidanza, Jacqueline A. et al., "Functionalization of Oligonucleotides by the Incorporation of Thio-Specific Reporter Groups", Methods in Molecular Biology, vol. 26, 1'994, pp. 121-143.
Gupta, Vineet, "Studies Aimed at Controlled Chemical Cleavage of DNA", Department of Chemictry—The College of Arts and sciences, University of Rochester, New York, 1997, 249 pages.
Hodges, Robin R. et al., "Post-Assay Covalent Labeling of Phosphorothiate-Containing Nucleic Acids with Multiple Fluorescent Makers", Biochemistry, vol. 28, 1989, pp. 261-267.
Qin, Peter Zhifeng et al., "Site-Specific Labeling of RNA with Fluorophores and Other Structural Probes", A Companion to Methods in Enzymology, No. 1'8, 1999, pp. 60-70.
Scheit, Karl Heinz, Dr., "Nucleoside Analogs", Synthesis and Biological Function, 1980, pp. 101-113.
Temsamani, Jamal et al., "Enzymatic Labeling of Nucleic Acids", Molecular Biology, vol. 5, 1996, pp. 223-232.
Trevisiol, Emmanuelle, et al., "Synthesis of Nucleoside Triphosphates that Contain an Aminooxy Function for Post-Amplification Labelling", Eur. Journal of Organic Chemistry, 2000, pp. 211-217.
"3D-Link™ Protocol Information", retrieved from the Internet on May 29, 2001, http://www.motorola.com/lifesciences/3dlprotocol. html, pp. 1-6.
"Alexa Fluor: Simply the Best and Brightest Fluorescent Conjugates," found on the internet at http://www.probes.com/media/publications/150.pdf.
Conway, E., et al., "The Covalent Attachment of Multiple Fluorophores to DNA Containing Phosphorothioate Diesters Results in Highly Sensitive Detection of Single-Stranded DNA", *Bioconjugate Chem.*, vol. 2, 1991, pp. 452-457.

* cited by examiner

Primary Examiner—Kenneth R. Horlick
Assistant Examiner—Cynthia Wilder
(74) Attorney, Agent, or Firm—Yonggang Ji

(57) ABSTRACT

An assay is provided for nucleic acids that can be post-synthetically labeled, wherein modified nucleoside triphosphates are used that are more efficiently and specifically incorporated during nucleic acid synthesis than labeled nucleoside triphosphates. In a preferred embodiment, nucleoside α-thiotriphosphates are utilized. Maleimide or iodoacetamide conjugating moieties can be attached post-synthetically. The conjugating moieties may include a reporter group. Also disclosed are new methods for detecting single nucleotide polymorphism.

8 Claims, 2 Drawing Sheets

US 7,223,538 B2

POST-SYNTHESIS LABELING OF NUCLEIC ACIDS, ASSAYS USING NUCLEIC ACIDS THAT ARE LABELED POST-SYNTHETICALLY, SINGLE NUCLEOTIDE POLYMORPHISM DETECTION, AND ASSOCIATED COMPOUNDS AND MICROARRAYS

FIELD OF THE INVENTION

This invention relates generally to the fields of biomolecule detection and nucleic acid synthesis, and more particularly to techniques for detecting and synthesizing nucleic acids, including associated compounds and biomolecule detection devices.

DESCRIPTION OF THE RELATED ART

Techniques to detect biomolecules, such as polynucleic acids and proteins, include the use of labels to enhance detection limits to a practical level. For example, a fluorophore label can be introduced enzymatically into the biomolecule of interest so that it can be detected via fluorescence. In nucleic acid synthesis, DNA and/or RNA polymerases can be used to incorporate either labeled primers or labeled nucleoside triphosphates into a polynucleotide chain. Nucleoside triphosphates substituted with a label or "reporter group" for such uses have been reported in Trevisiol, E., et al., Synthesis of Nucleoside Triphosphates that Contain an Aminooxy Function for "post-Amplification Labeling", Eur. J. Org. Chem., 2000, 211-17; Fidanza, et al., Functionalization of Oligonucleotides by the Incorporation of Thio-Specific Reporter Groups, Methods in Molecular Biology, Volume 26, Protocols for Oligonucleotide Conjugates: Ed. Agrawal, S., 1994, 121-143; Temsamani, J. et al., Enzymatic Labeling of Nucleic Acids, Molecular Biotechnology 1996, 5, 223-32;b) Qin et al., Site-Specific Labeling of RNA with Fluorophores and Other Structural Probes, Methods: A Companion to Methods in Enzymology 1999, 18, 60-70; Hodges, R. R. et al., "Post-Assay" Covalent Labeling of Phosphorothioate-Containing Nucleic Acids with Multiple Fluorescent Markers, Biochemistry 1989, 28 261-67.

Additional background information can be found in U.S. Pat. No. 4,908,307 to Rodland et al.; U.S. Pat. No. 5,545,531 to Rava et al; U.S. Pat. No. 5,702,925 to Smith et al.; U.S. Pat. No. 5,741,644 to Kambara et al.; U.S. Pat. No. 5,804,375 to Gelfand et al.; U.S. Pat. No. 5,858,659 to Sapolsky et al.; U.S. Pat. No. 6,087,095 to Rosenthal et al.; and U.S. Pat. No. 6,183,970 to Okano et al., as well as PCT Publications Nos. WO 98/56954 to Chee; WO 00/39345 to Makrigiorgos; and WO 00/79006 to Petersdorf, and in the following documents: Conway et al., "The Covalent Attachment of Multiple fluorophores to DNA Containing Phosphorothioate Diesters Results in Highly Sensitive Detection of Single-Stranded DNA," Bioconjugate Chem., Vol. 2, No. 6, pp. 452-457, 1991; Eckstein, F., "Nucleoside Phosphorothioates", Ann. Rev. Biochemistry, 54:367-402, 1985; Fidanza et al., "Introduction of Reporter Groups at Specific Sites in DNA," J. Am. Chem. Soc., 111, pp. 9117-9119, 1989. Gupta, V., "Studies Aimed at Controlled Chemical Cleavage of DNA," Department of Chemistry—The College of Arts and Sciences, University of Rochester, N.Y., 1997; and Scheit, "Nucleotide Analogs," Synthesis and Biological Function, pp. 101-113, 1980.

Hybridization Assays

In a hybridization assay, such as an expression assay, DNA or RNA target molecules are hybridized to probes. Typically, either the target nucleic acid or the probe is labeled using base-modified nucleoside triphosphates, such as 5-Cy3-dUTP, 5-Cy3-dCTP, 5-TMR-dUTP, and 7-biotin-7-deaza-dATP (phosphorylated nucleosides are also referred to as nucleotides). The nucleoside triphosphates are modified at various positions, such as on the base or sugar. However, the rate and efficiency of enzymatic incorporation of a modified nucleotide into the synthesized polynucleotide depends on the label and where it is located on the modified nucleotide. To increase the efficiency of target or probe production, it is beneficial to use modified nucleotides that are efficiently incorporated into the synthesized polynucleotide. Examples of hybridization assays include uses of nucleic acid arrays, Southern blotting, Northern blotting, and FISH.

Single Nucleotide Polymorphism Detection

The genes of an individual within a population will vary in sequence with that of the genes of any other individual within the population. The bulk of these variations contribute to individuality within the population. Often these variations can be mapped to a change in a single nucleotide at a certain position. Methods of detecting these single nucleotide polymorphisms (SNP) are useful for determining the genotype and potentially subsequent phenotype of an individual. Many methods of detecting SNPs have been developed. (Walburger et al., Mutat Res 2001 January;432(3-4): 69-78; Kozlowski and Krzyzosiak, Nucleic Acids Res Jul. 15, 2001;29(14):E73-3; Zhang et al., Anal Chem May 1, 2001;73(9):2117-25; Lareu et al., Forensic Sci Int May 15, 2001;118(2-3):163-8; Beaudet et al., Genome Res 2001 April;11(4):600-8)

In one such method, SNP detection technology uses a chain-terminating nucleotide (e.g., 2', 3'-dideoxynucleotide, acyclonucleotides) that is linked to a detectable group, such as a fluorescent label. The specificity and efficiency of enzymatic incorporation of such nucleotides, especially with modifications to the sugar (e.g., a 2', 3'-dideoxy NTP, or an acyclo NTP) and the base (carrying the fluorophore), is considerably lower. Poor incorporation reduces the signal intensity of such assays.

Thus, there is a need for improved assays, kits, and technologies for detecting biomolecules, such as nucleic acid oligomers and polymers and peptides and proteins.

BRIEF SUMMARY

Nucleic Acid Assay

In an embodiment, an assay and kit is provided for the enzymatic synthesis and detection of nucleic acids that can be post-synthetically labeled, wherein modified nucleoside triphosphates are used that are more efficiently and specifically incorporated during nucleic acid synthesis than labeled nucleoside triphosphates. The modified nucleoside triphosphates are preferably non-radio-labeled and incorporated with approximately the same efficiency and specificity as unmodified nucleotides. In a preferred embodiment, nucleoside α-thiotriphosphates are utilized. The synthesis technique can be used for cRNA, cDNA, and other compounds. The phosphorothioate thio moiety in the resulting oligomer or polymer is capable of reacting with a thioreactive compound, which may include a label or which may bind to a label.

Single Nucleotide Polymorphism (SNP) Assay

In an embodiment of the present invention, probes in a single base extension (SBE) assay can be labeled by utilizing either a dideoxy or acyclo thionucleotide or other appropriate chain-terminating compounds in the extension reaction in which the incorporated compound residue will react with a thioreactive compound. The chain terminating nucleotides are preferably non-radio-labeled, and incorporated with approximately the same efficiency and specificity as chain terminating nucleotides that do not contain a moiety that will react with a thioreactive compound post-synthetically. Only the extended probes that contain a residue with the moiety that will react with a thioreactive compound (e.g., contain a thio moiety) will be labeled during subsequent reaction with a thioreactive compound.

Better quantitation results from the polynucleotide and SNP detection assays of the present invention as the various modified nucleotides are incorporated at a similar level.

Microarrays

Nucleic acids produced in accordance with an embodiment of the present invention can be hybridized to probes on microarrays (also referred to as probe chips, biochips, and similar terms) to create new microarray products. In an embodiment, nucleic acids and other synthesis products produced in accordance with the present invention are labeled prior to hybridization with the microarray probes, while in another embodiment, labeling is done post hybridization. In an embodiment, a microarray is disclosed having a probe terminated by a non-radio-labeled dideoxynucleoside thiophosphate, or an acyclonucleoside thiophosphate residue.

New Nucleic Acids and Nucleotides

Novel nucleic acids are disclosed that contain residues of at least three or at least four different nucleoside thiophosphates. Also disclosed are non-radio-labeled dideoxynucleoside α-thiotriphosphates, and acyclonucleoside α-thiotriphosphates, methods for synthesizing same, and nucleic acids containing a terminal non-radio-labeled dideoxynucleoside thiophosphate or an acyclonucleoside thiophosphate. The following illustrative figures and detailed description further supplement the preceding invention summary.

DETAILED DESCRIPTION

Nucleoside Triphosphates

Figure 1:
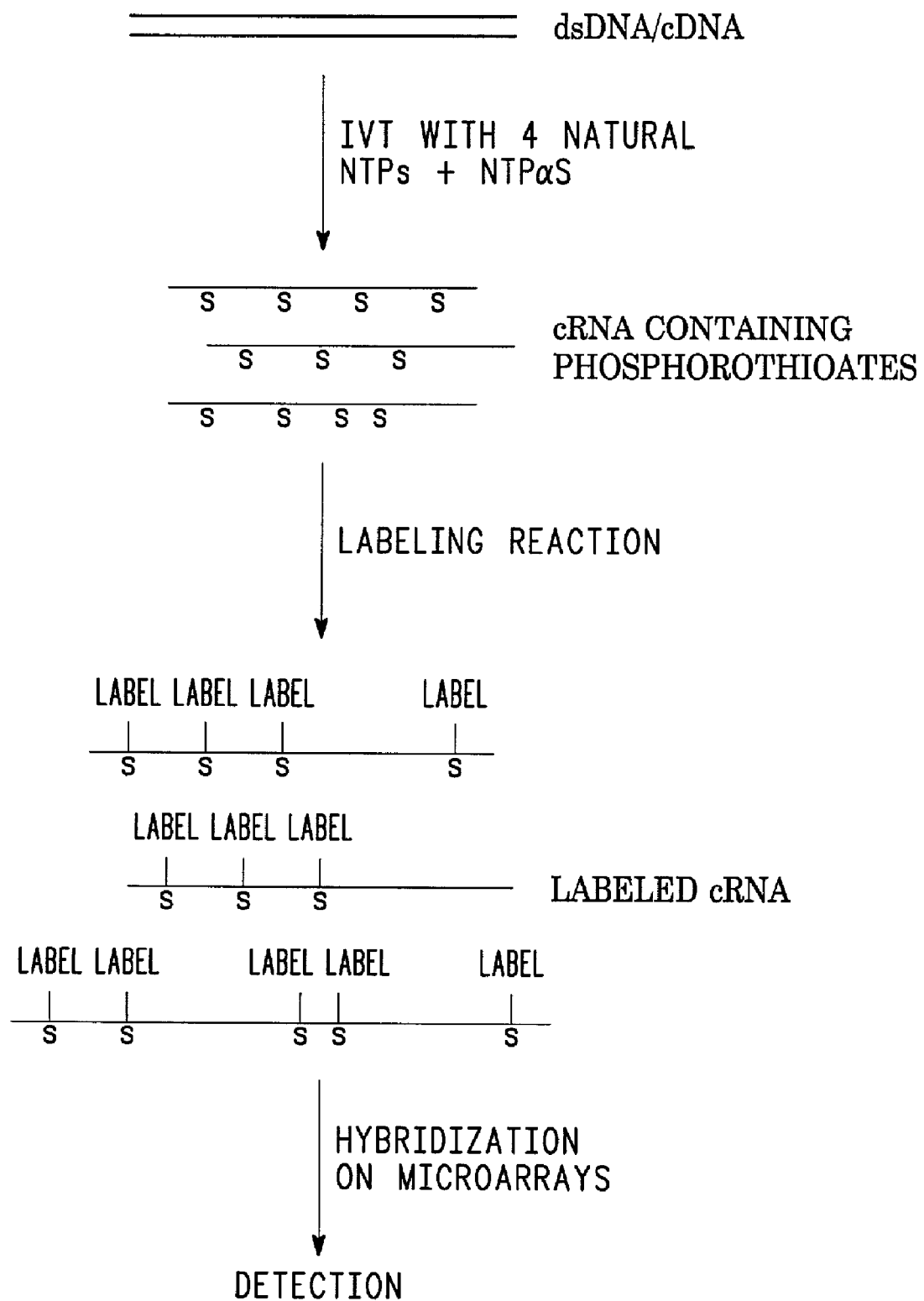
FIG. 1 is a diagram illustrating a new expression assay conducted in accordance with the present invention.

Non-limiting examples of modified nucleoside triphosphates for use with the present invention include α-thio triphosphates, for example adenosine α-thiotriphosphate, cytidine α-thiotriphosphate, guanosine α-thiotriphosphate, thymidine α-thiotriphosphate, and uridine α-thiotriphosphate, as well as analogs thereof (e.g., 2-amino-A). When the bases adenine, guanine, cytosine, uracil and thymine are incorporated into a nucleoside or nucleotide, their respective spellings are commonly changed to adenosine, guanosine, cytidine, uridine, and thymidine.

In an embodiment of the present invention, thio-substituted nucleoside triphosphates having the following formula are used:

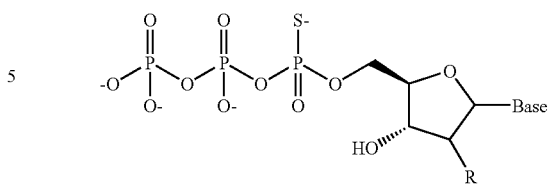

R may be OH, H, $NH_2$, F, $OCH_3$, or $OCH_2CH_2OCH_3$. Preferred thio-substituted nucleoside triphosphates ("sNTP" or "α-thio NTPs") in accordance with the present invention are those compounds that will react in a substantially similar fashion to naturally occurring NTPs in the synthesis of nucleic acids, such as ribonucleic acid (RNA) or deoxyribonucleic acid (DNA) polymers or oligomers. Thus, a preferred thio-substituted polynucleotide in accordance with the present invention would have the formula:

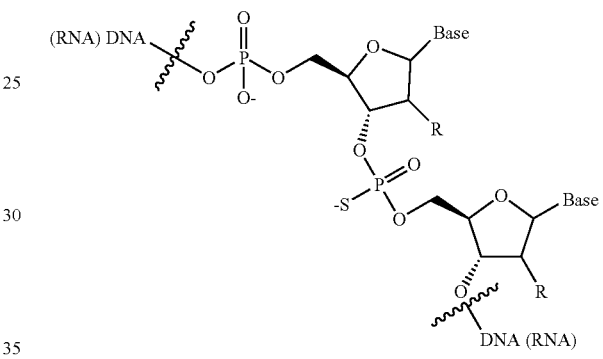

Dideoxy- and Acyclo-Nucleotides

In the new single nucleotide polymorphism assay of the present invention, dideoxynucleoside α-thio triphosphates (i.e., A, T, C, G, and analogs thereof) are utilized, as the dideoxynucleotide lacks a 3' hydroxyl group, and therefore prevents further chain elongation upon incorporation into a growing polynucleotide. Preferred dideoxynucleotides are non-radio-labeled.

Methods of producing thio-substituted dideoxynucleoside triphosphates are known (Krieger et al., "Synthesis and biological applications of 2', 3'-dideoxynucleoside-5'-O-(α-thio)triphosphates," *Nucleosides Nucleotides* 8(5-6):849-53 (1988); incorporated herein by reference).

Also, disclosed herein are acyclonucleoside α-thio triphosphates (i.e., A, T, C, G, [U] and analogs thereof). Methods of producing acyclo nucleotides are well known in the art. (Gao and Mitra, "Synthesis of Acyclovir, Ganciclovir and Their Prodrugs: A Review," *Synthesis Stuttgart* 3:329-351 (2000); Harnden and Serafinowska, "Synthesis and Properties of S-Phosphates of Some Antiviral Acyclonucleosides," *Nucleosides and Nucleotides* 13(4):903 (1994); both incorporated by reference).

Labels and Conjugating Moieties

The term "label" is used to refer to any chemical group or moiety having a detectable physical property or any compound capable of causing a chemical group or moiety to exhibit a detectable physical property, such as an enzyme that catalyzes conversion of a substrate into a detectable product. The term "label" also encompasses compounds that inhibit the expression of a particular physical property. The label may also be a compound that is a member of a binding pair, the other member of which bears a detectable physical property.

Preferred nucleic acids produced in accordance with the present invention contain at least one residue having a moiety that will conjugate to a thioreactive compound. Preferred SNP probes produced in accordance with the present invention terminate with a residue having a moiety that will conjugate to a thioreactive compound. A conjugating moiety may be a thioreactive compound that includes a label or which may bind to a label. The thioreactive compound may include an electrophilic group. Nonlimiting examples of electrophiles for use with the present invention include alkyl iodides, maleimides, arylmethyl halides, iodoacetamides, bromoethyl ketones, and bromobimane, which can react with and conjugate to phosphorothioates and act as conjugating moieties to biological molecules, such as fluorescent dyes. In another embodiment, preferred nucleophiles incorporate a label or reporter moiety. Without limiting the invention to any particular theory or mechanism, it is believed that phosphorothioate linkages in a nucleic acid react with a high degree of specificity with certain nucleophiles, such as iodoacetamides and maleimides.

In an embodiment, maleimides are preferred over iodoacetamides. Preferred iodoacetamides and maleimides with labels, or "reporter groups," include TMR-maleimide, TMR-iodoacetamide, and Alexafluor-maleimide (all available from Molecular Probes). TMR is an abbreviation for N,N,N',N'-tetramethyl-6-carboxyrhodamine. In an embodiment, TMR dyes are preferred over the Alexafluor dye.

The formula for TMR-iodoacetamide is shown below.

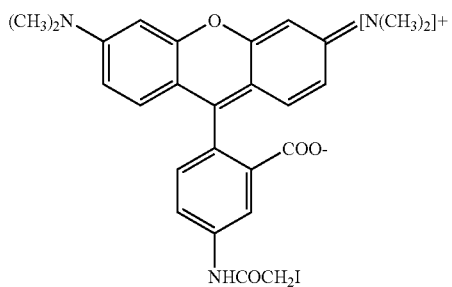

The formula for TMR-maleimide is shown below.

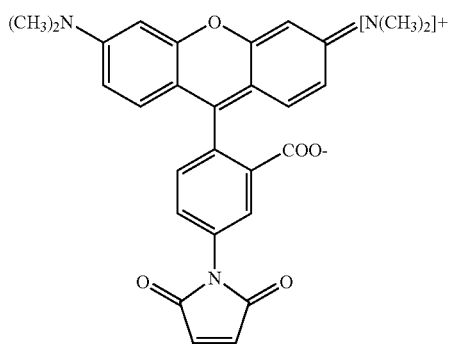

Reaction of a dye-labeled iodoacetamide with a thio-substituted polynucleotide of the present invention is illustrated below. The reaction may be performed under a variety of conditions. For example, the pH may be between 6 and 12 with 8-9.5 being preferred. Borate, carbonate, or phosphate buffers may be used at a concentration of 1-100 mM with 50 mM being preferred. The temperature may be from 15° C. to 50° C. with ambient temperature being preferred. Also, it is preferable that the reaction take place in the dark. Furthermore, solvents such as DMF and DMSO may be used as necessary.

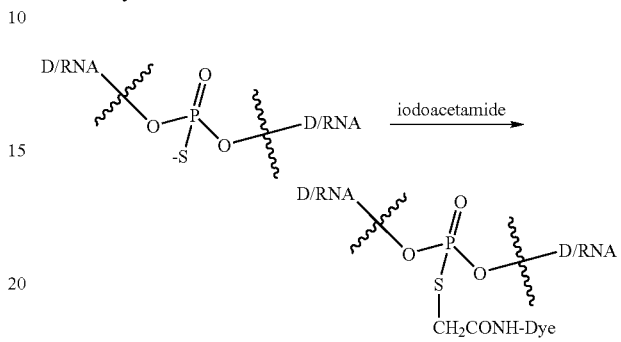

Reaction of a dye-labeled maleimide with a thio-substituted polynucleotide of the present invention is illustrated below.

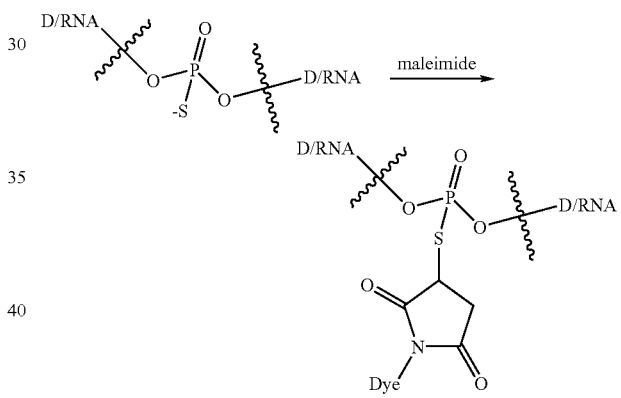

Nucleic Acid Sythesis and Labeling

The term "nucleic acid(s)" is used to refer to deoxyribonucleic acid (DNA) and ribonucleic acid (RNA) in any form, including inter alia, single-stranded, duplex, triplex, linear and circular forms. It also includes polynucleotides, oligonucleotides, chimeras of nucleic acids and analogues thereof. The modified nucleic acids described herein can be composed of the well-known deoxyribonucleotides and ribonucleotides, composed of the bases adenine, cytosine, guanine, thymine, and uracil, or may be composed of analogues or derivatives of these bases, appropriately modified to permit post-synthesis labeling in accordance with the present invention.

In the first step of an exemplary nucleic acid synthesis and labeling embodiment, a polynucleotide is synthesized that incorporates one or more nucleoside thiophosphate residues, such as but not limited to those formed by reaction with adenosine α-thiotriphosphate, cytidine α-thiotriphosphate, guanosine α-thiotriphosphate, thymidine α-thiotriphosphate, and/or uridine α-thiotriphosphate. In an embodiment, at least three, and more preferred four, of the group consisting of adenosine α-thiotriphosphate, cytidine α-thiotriphosphate, guanosine α-thiotriphosphate, thymidine α-thiotriphosphate, and uridine α-thiotriphosphate are included in the synthesis reaction.

In a second or nucleophilic reaction step, the polynucleic acid is reacted with a nucleophile, such as but not limited to an iodoacetamide or a maleimide. In a third or labeling step, the nucleophilic reaction step products are conjugated to a detectable moiety, such as a fluorescent dye. The third step can be eliminated if the nucleophiles are conjugated to a label prior to reaction with the synthesized nucleic acid. Thus, cRNA transcripts, or cDNA, can be conjugated with a variety of labels post-synthetically.

Detection

Labeled polynucleotides produced in accordance with the present invention can be detected using essentially any method for detecting polynucleotides. Preferably, the labeled nucleotide is detected by hybridization with a polynucleotide comprising at least a portion that is complementary to the labeled nucleotide. In preferred embodiments, hybridization is performed under stringent conditions. Most preferably, detection uses microarray technology or a microfluidic device. For example, the synthesized thio cDNA or cRNA (i.e., nucleic acid incorporating one or more thio nucleotide residue(s)) can be hybridized to a probe on a microarray, and detected by detecting the signal generated by the labels, e.g., fluorescence. Other non-limiting examples of detection moieties that may be used post-synthetically include redox moieties such as ferrocene, and electrochemically active agents such as ruthenium complexes.

It is preferred that the resulting nucleic acid oligomers and polymers will hybridize to complementary DNA or RNA strands in substantially the same fashion as nucleic acid oligomers and polymers containing only naturally occurring NTPs (i.e., NTP residues). It is understood that polynucleic acids may under certain circumstances known to those of skill in the art bind to peptide or polypeptide sequences, and such uses of the present invention are contemplated and incorporated herein. For example, nucleic acids of the present invention may be used in SELEX technology (U.S. Pat. No. 5,567,588; incorporated herein by reference). Nucleic acids that incorporate polypeptides and other moieties are likewise contemplated and incorporated into the present invention.

In an embodiment, labels are conjugated to thio-substituted nucleic acid oligomers and polymers prior to or after hybridization to complementary DNA or RNA strands. Thus, for example, a electrophilic group may be reacted with the thio-substituted polynucleotide, wherein the electrophile may be preconjugated to a reporter group to create a labeled polynucleotide, or an intermediate conjugating moiety can be attached to the polynucleotide thio-substituent(s), followed by reaction, either before or after hybridization, with a label. It is contemplated that more than one type of label or conjugating intermediate may be coupled to the polynucleotides synthesized in accordance with the present invention. Examples of conjugating intermediates include haptens (antibody), biotin (avidin/streptavidin), and ligands (receptor).

Microarrays

High density arrays of oligonucleotides, peptides and other polymer sequences on solid substrates are commercially available. In a preferred embodiment, the microarray is a 3D hydrogel array. Hydrogel arrays are commercially available (CODELINK; Motorola Life Sciences, Northbrook, Ill.). Methods of making hydrogel arrays and attaching nucleic acids to such arrays are described in WO 01/01143(incorporated herein by reference in its entirety).

Alternatively to hydrogel arrays, an oligonucleotide array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques. See also, Fodor et al., Science, 251, 767-77 (1991); U.S. Pat. No. 5,700,637; U.S. Pat. No. 6,054,270. These procedures for synthesis of polymer arrays are now referred to as VLSIPS (very large scale immobilized polymer synthesis) procedures. Using the VLSIPS approach, one heterogenous array of polymers can be converted, through simultaneous coupling at a number of reaction sites, into a different heterogenous array. Lockhart et al. in U.S. Pat. No. 6, 040,138, describe the use of oligonucleotide arrays to analyze the expression of a multiplicity of genes and the construction of such arrays.

In a preferred embodiment, 3D-Link™ Activated Slides (available from Motorola Life Sciences, Northbrook, Ill., USA) can be used as substrates for immobilizing probes to form microarrays.

New Expression Assay Method

With reference to FIG. 1, a diagrammatic depiction of the steps in an expression assay conducted in accordance with the present invention is illustrated. Starting at the top of the diagram, a DNA template is used to perform in vitro transcription (IVT) with 4 natural nucleoside triphosphates and α-thio nucleoside triphosphates. The reaction is optimized to maximize synthesis, achieve desired chain length, minimize label interactions such as quenching, and/or to economize on α-thio reagents. The resulting cRNA containing phosphorothioates is then reacted with a label and the labeled cRNA is then hybridized onto a microarray with appropriate stringency and washing conditions. The bound labeled cRNA is then detected. Alternatively, the cRNA containing phosphorothioates can be first hybridized onto the microarray and these resulting hybridized pairs then reacted with the label. Additionally, the reaction products can be analyzed in a microfluidic device.

Single Nucleotide Polymorphism Detection

In certain embodiments of the present invention, one or more α-thio substituted nucleotides are used in methods of detecting single nucleotide polymorphisms (SNPs). SNP detection allows comparisons of a large number of genes between individuals within a population. Several methods of detecting SNPs are known in the art (Kwok P. Y., "High-throughput genotyping assay approaches," *Pharmacogenomics* 1(1):95-100 (2000); incorporated herein by reference). Such different methods include allele-specific hybridization techniques, allele-specific primer extension techniques, allele-specific oligonucleotide ligation techniques, and allele-specific cleavage of a flap probe techniques. In light of the present disclosure, one of skill in the art would recognize that the compositions and methods of the present invention may be utilized in any of the above methods.

Figure 2:
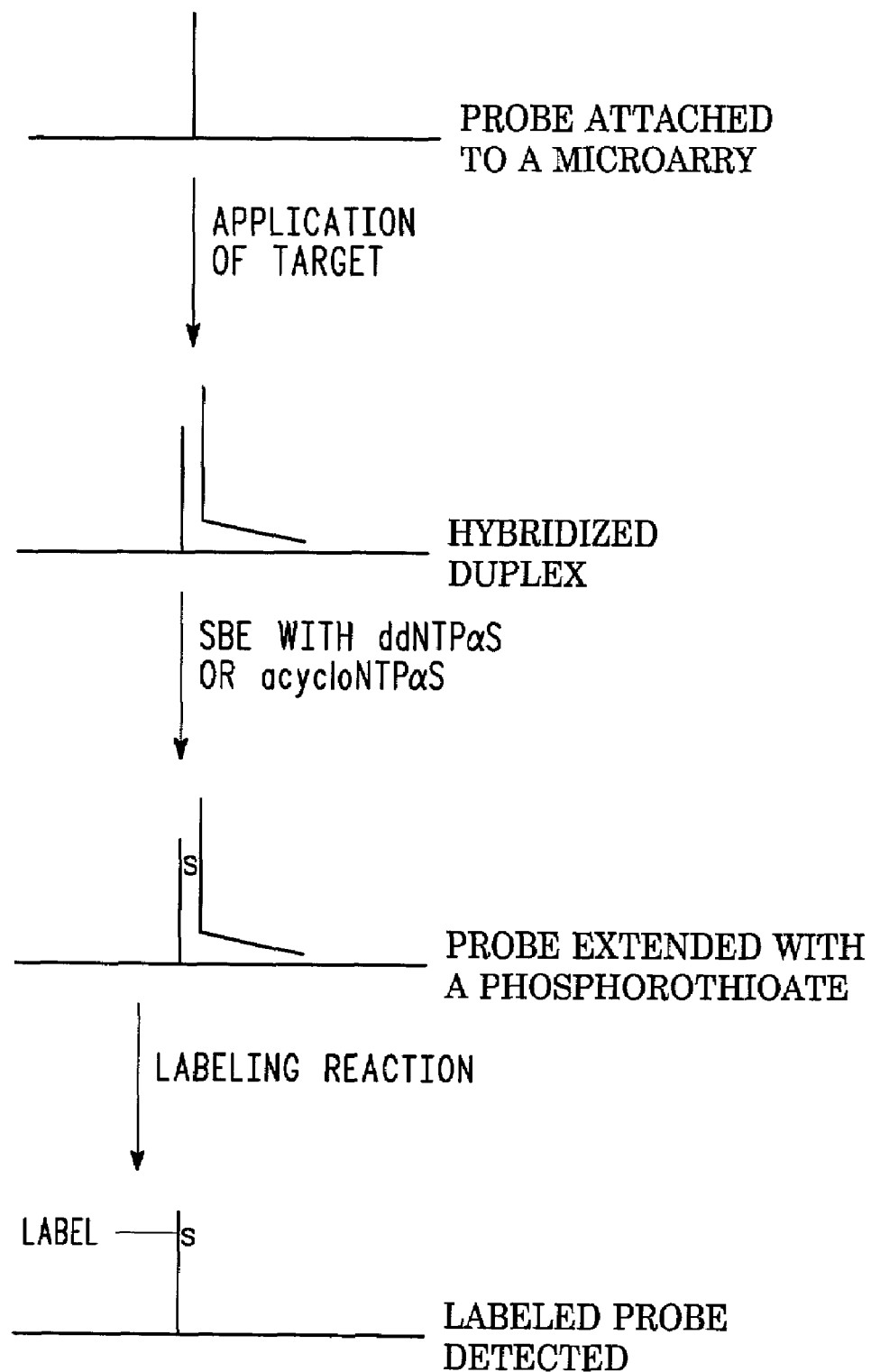
FIG. 2 is a diagram illustrating a new SNP assay conducted in accordance with the present invention.

In a preferred embodiment, an allele-specific primer extension technique is utilized. With reference to FIG. 2, a diagrammatic depiction of the steps for SNP detection conducted in accordance with the present invention is illustrated. Starting at the top of the diagram, a probe is attached to a microarray, and a target applied to the microarray. Target and probe form a hybridized duplex. Single base extension (SBE) is then conducted preferably using an α-thio-substituted dideoxynucleotide (e.g., ddNTPαS) or acyclo compound (e.g., acycloNTPαS) to extend the probe. Of course, in some embodiments more than one nucleotide may be incorporated, in which case non-terminating nucleotides (dNTPs) are used along with the dideoxy- or acyclo-α-thio nucleotide. Thereafter, a labeling reaction is performed to label the probe. In a preferred embodiment, dye-labeled maleimide is used as a reactive label for the SNP assay. The labeled probe is then detected using standard techniques known to one of skill in the art.

In another embodiment, a proble is hybridized to the target containing the SNP, where the SNP base is at the position one base beyond the 3' end of the probe. By having four separated probes, each of the same sequence, and adding targets, polymerase, and one of the four labeled ddNTPs, it is possible to identify the SNP by which ddNTP causes the probe to fluoresce due to incorporation of the nucleotide. This method is more fully described in U.S. Pat. No. 5,679,524, "Ligase/polymerase mediated genetic bit analysis of single nucleotide polymorphisms and its use in genetic analysis," to Nikiforov et al. A preferred embodiment using this technique would entail tagging a thio ddNTP with the thio reactive dye.

In an embodiment, at least four of the group consisting of dideoxyadenosine α-thiotriphosphate, dideoxycytidine α-thiotriphosphate, dideoxyguanosine α-thiotriphosphate, dideoxythymidine α-thiotriphosphate, and dideoxyuridine α-thiotriphosphate are added to the probe extension reaction. The probes are then labeled, the microarray treated to denature the labeled probes hybridized to the target, and the probes detected.

Hybridization

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label.

It is generally recognized that nucleic acids are denatured by increasing the temperature or by decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency. Furthermore, one of skill in the art would recognize that the length and G:C content of the hybridizing portions of the molecules should be considered when determining proper denaturation or hybridization conditions.

Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)). In a preferred embodiment, hybridization is conducted in accordance with procedures contained in "3D-Link™ Protocol Information," Motorola Life Sciences, Northbrook, Ill., USA (2001).

Signal Detection

Means of detecting labeled target (sample) nucleic acids hybridized to microarray probes are known to those of skill in the art. Thus, for example, a calorimetric label may be visualized directly when sufficient labeled sample is present. Radioactive labeled probes can be detected with photographic film or a solid state detector.

In a preferred embodiment, the target nucleic acids are labeled with a fluorescent label and detected using standard methods known to those of skill in the art. For example, the localization of the label on an array can be accomplished with a microscope. The hybridized array can be excited with a light source at the excitation wavelength of the particular fluorescent label and the resulting fluorescence at the emission wavelength detected. For example, the excitation light source may be a laser appropriate for the excitation of the fluorescent label. Detection may be automated with a computer-controlled stage to automatically scan the entire array. Additional equipment, such as a phototransducer (e.g., a photomultiplier, a solid state array, a camera, etc.) attached to an automated data acquisition system may be used to automatically record the fluorescence signal. Such automated systems are described at length in U.S. Pat. No. 5,143,854 and PCT application WO 92/10092.

EXAMPLES

In order to find optimal nucleophiles and labels for the new α-thio nucleotides of the present invention, experiments were conducted using cRNA synthesized in accordance with the present invention, followed by labeling reactions with various dyes.

Example 1

Synthesis of cRNA

A linearized plasmid DNA was used as a template for the in vitro transcription (IVT) reaction, which has a SP6 RNA polymerase promoter. Cy3-labeled cRNA was synthesized by incubating 1 μg of DNA in the presence of ATP (5 mM), GTP (5 mM), CTP (3.75 mM), UTP (3.75 mM), Cy3-UTP (0.5 mM) and Cy3-CTP (0.5 mM), in 10×reaction buffer (Gibco) and SP6 RNA polymerase (kit from Ambion). The mixture was incubated at 37° C. for 6 hours, then purified using RNeasy columns (from Qiagen). Phosphorothioate-cRNA was synthesized by substituting Cy3-labeled nucleoside triphosphates with either one or all four α-thio nucleoside triphosphates (obtained from Amersham Biosciences, also available from PerkinElmer) at a concentration of 1.5 mM. Natural cRNA was prepared using only natural nucleotides at 5 mM each. The synthesized RNA was fragmented using established protocols (i.e., treated with 30 mM $Mg^{2+}$ at 94° C. for 15 minutes).

Prophetic Example 2

Labeling with Reactive Dyes

Three different compounds were tested as labeling dyes: TMR-maleimide (formula shown previously), TMR-iodoacetamide (formula shown previously), and Alexafluor-maleimide (obtained from Molecular Probes). A sample of cRNA (40 μg in 30 μL of 10 mM Tris.Cl, at pH 8.0) was treated with reactive dyes solutions (10 mM in DMF) to a final concentration of 1 mM. The mixture was kept at 50° C. for 24 hours, and the unreacted dye removed using microspin G-6 columns (Amersham). The cRNA product was used directly in hybridization experiments on microarrays following the procedures in "3D-Link™ Protocol Information," Motorola Life Sciences, Northbrook, Ill., USA (2001).

Example 3

Gel Analysis

Ten samples, as described in Table 1 below, were run on a 1% agarose gel.

TABLE 1

SAMPLES 1–10 RUN ON GEL

| LANE | SAMPLE |
|---|---|
| 1 | 1 kb DNA ladder (from Promega) |
| 2 | Cy3-cRNA |
| 3 | Phosphorothio-cRNA-NO DYE |
| 4 | Phosphorothio-cRNA-NO DYE |
| 5 | Phosphorothio-cRNA-NO DYE |
| 6 | Natural cRNA-TMR-iodoacetamide |
| 7 | Phosphorothio-cRNA-TMR-iodoacetamide |
| 8 | Phosphorothio-cRNA-TMR-maleimide |
| 9 | Phosphorothio-cRNA-Alexafluor Dye |
| 10 | Natural cRNA-TMR-maleimide |

Initially, the gel was not stained, and an image taken using a Fluorimager using Cy3-settings. The gel was then stained with ethidium bromide (EtBr), and analyzed using EtBr-settings. The gel images showed that natural cRNA that does not contain any phosphorothioates does not get labeled with maleimide. In samples 3-5, the phosphorothioate-cRNA was not labeled, whereas in samples 7-9, the phosphorothioate-cRNA was labeled. The gel images showed that phosphorothioate-cRNA is labeled only after treatment with the alkylating dyes.

Further, the TMR-maleimide dye selectively labels phosphorothio-cRNA (sample 8) over natural cRNA (sample 10). Although TMR-iodoacetamide showed selectivity in labeling phosphorothio-cRNA (sample 7) over natural cRNA (sample 6), the differential was not as great as for the TMR-maleimide results.

Prophetic Example 4

Microarray Analysis

Analysis of cRNA on DNA microarrays was performed. Three microarrays were prepared: (1) by hybridizing cRNA labeled with Cy3-nucleoside triphosphates during in vitro transcription onto an Expression Analysis BioChip, (2) by hybridizing thio cRNA, which was post-synthetically labeled with TMR-maleimide, onto an Expression Analysis BioChip, and (3) by hybridizing natural unlabeled cRNA, which was post-synthetically labeled with TMR-maleimide, onto an Expression Analysis BioChip.

The microarray analysis demonstrated that the post-synthesis labeling of cRNA synthesized with α-thio-nucleoside triphosphates using TMR-maleimide is as or more effective than cRNA synthesized with direct Cy-3 nucleotide incorporation. The analysis clearly demonstrated that non-specific labeling of natural cRNA with TMR maleimide is very limited as essentially no fluorescence pattern is generated after hybridization to the microarray.

Example 5

Microarrays and Kits

Templates for probes are commercially available. For example, sets of certain human genes can be obtained from Motorola Life Sciences, Northbrook, Ill., USA. Probes can be prepared and immobilized on substrates to form microarrays. In vitro transcription can be performed on biosamples in the accordance with the present invention (e.g., using thio nucleotides). For example, nucleic acid targets having thio nucleotide residues can be labeled, hybridized to probes on a microarray, and detected.

Exemplary expression assay kit components are shown in Table 2:

TABLE 2

EXPRESSION ASSAY KIT

| INGREDIENT | SOURCE/COMMENTS |
|---|---|
| Natural NTPs | APB |
| α-thio NTP reagent | APB |
| Microarray substrate | Motorola Life Sciences |
| Label-Thioreactive compound | Molecular Probes |
| Buffer | Motorola |
| Fragmentation Buffer | Ambion |
| Stop Buffer | Ambion |
| Precipitation Solution | Ambion |
| T7 Transcription System | Ambion |
| RNase-free Dnase | Ambion |
| Control mRNA | Ambion |
| Control plasmid | Ambion |

Preferred expression assay kits contain at least two of the following components: microarray substrate (with or without probes attached), label, and α-thio NTP reagent.

An SNP detection kit for using SBE would include at least two of the following components: non-radio-labeled α-thio dideoxy NTP or α-thio acyclo NTP reagent, label reagent, and a microarray substrate. Probes may be attached to the substrate to form a microarray. The labels may be different for the SNP kit from the expression kit.

The new expression assay of the present invention provides numerous advantages. For example, cRNA transcripts (or cDNA) can be labeled with a variety of detection moieties post-synthetically. The labeled cRNA can be detected using standard microarray technology or in a microfluidic device. Each molecule of cRNA and/or cDNA can be labeled approximately equally, since it will have approximately the same number of α-thiophosphate linkages. This labeling methodology can give a better estimate of relative expression levels of different genes and thus permit better "single molecule counting." Unlike current methods that use only CTP or TTP analogues, α-thio nucleoside triphosphates of all four natural nucleotides can be used in the same reaction. Thus, nucleic acids are disclosed comprising at least three or four residues of the group consisting of an adenosine thiophosphate residue, a cytidine thiophosphate residue, a guanosine thiophosphate residue, a thymidine thiophosphate residue, and a uridine thiophosphate residue (The term residue is used herein to refer to the incorporated form of the monomers used to form a polymer). Further, nucleophilic substituted and labeled forms thereof are disclosed hereby.

Multiple dye labeling schemes are possible since the labeling is done post-synthetically. For example, in an embodiment, some labeled nucleotides can be incorporated during synthesis along with α-thio nucleoside triphosphates.

Further, cRNA or cDNA produced in a single reaction can be used in a number of different labeling and detection applications. For example, the polynucleotide sample can be divided and treated differently.

In the new single nucleotide polymorphism detection assay of the present invention, only the extended probes that contain an α-thio residue will be labeled during the post-synthesis dye reaction. Since incorporation of all of the modified nucleotides can be controlled at a similar level, better quantitation will result.

While embodiments of the present invention have been disclosed as examples herein, there could be a wide range of changes made to these embodiments without departing from the present invention. Thus, it is intended that the foregoing detailed description be regarded as illustrative rather than limiting and that it be understood that it is the following claims, including all equivalents, which are intended to define the scope of the invention.

What is claimed:

1. In a nucleic acid expression assay, comprising (1) performing in vitro transcription of target nucleic acid template to generate cRNA, (2) contacting said cRNA with a probe immobilized on a microarray under conditions that allow hybridization between said cRNA and said probe, and (3) detecting hybridized cRNA to assay expression of said target nucleic acid template, the improvement comprising, (a) during said performing step, incorporating in said cRNA at least one phosphorothioate moiety; and (b) labeling said cRNA by conjugating a reporter molecule to said phosphorothioate moiety wherein said labeling step comprises reacting said target nucleic acid with a conjugating moiety that specifically reacts with said phosphorothioate moiety, followed by reaction with a labeling moiety that specifically reacts with said conjugating moiety.

2. The method of claim 1, wherein said labeling step follows said contacting step.

3. The method of claim 1, wherein said reporter molecule has an electrophilic moiety.

4. The method of claim 1, wherein said conjugating moiety is an electrophilic moiety.

5. The method of claim 3, wherein said electrophilic moiety is selected from the group consisting of a maleimide and an iodoacetamide.

6. The method of claim 1, wherein said reporter molecule is selected from the group consisting of a fluorophore, a redox moiety, and an electrochemically active agent.

7. The method of claim 1, wherein said reporter molecule is selected from the group consisting of TMR-maleimide, TMR-iodoacetamide and ALEXAFLUOR-maleimide.

8. The method of claim 1, wherein said cRNA has at least three different thio ribonucleotides, said thio ribonucleotides being selected from the group consisting of an adenosine thiophosphate, a cytidine thiophosphate, a guanosine thiophosphate, a thymidine thiophosphate, and a uridine thiophosphate.

* * * * *